United States Patent [19]

Müller et al.

[11] Patent Number: 5,185,326
[45] Date of Patent: Feb. 9, 1993

[54] EFOMYCINS A, E AND G AS ANTIINFLAMMATORY AGENTS

[75] Inventors: Hartwig Müller, Velbert; Erwin Bischoff, Wuppertal; Burkhard Fugmann, Wuelfrath; Karlheinz Weber; Klaus Frobel, both of Wuppertal; Bruno Rosen, Wuelfrath; Rudi Grützmann, Solingen, all of Fed. Rep. of Germany; Guenther Karmann, West Haven, Conn.; Christian Kohlsdorfer, Erftstadt, Fed. Rep. of Germany

[73] Assignee: Bayer Aktiengesellschaft, Leverkusen, Fed. Rep. of Germany

[21] Appl. No.: 709,902

[22] Filed: Jun. 3, 1991

[30] Foreign Application Priority Data

Jun. 14, 1990 [DE] Fed. Rep. of Germany ....... 4019024

[51] Int. Cl.$^5$ .................. A61K 31/70; A61K 31/71
[52] U.S. Cl. .............................. 514/23; 514/53; 514/25; 536/7.1
[58] Field of Search .................. 514/23, 53, 25; 536/1.1, 7.1

[56] References Cited

U.S. PATENT DOCUMENTS 4,927,810  5/1990  Frobel et al. .................. 514/23

FOREIGN PATENT DOCUMENTS 03144863  5/1989  European Pat. Off. .
0346078  12/1989  European Pat. Off. .

OTHER PUBLICATIONS

Karger Reprint, Article, "Influence of Calcium on the In Vivo Flow of Leukocytes and Erythrocytes", B. Rosen, pp. 68-86.
Abstract sheet of Journal article, ND: 90147276, Ti: "The state of leykocyte adhesivesness . . . ".
Abs. sheet of J. article, ND: 89351110, Ti: "Increased expression of P150,95 and CR3 leukocyte adhesion . . . ".
Abs. sheet of J. article, ND: 83130952, Ti:"Polymorphonuclear leuk . . . ".
Abs. sheet of J. article, ND: 85092333, Ti: "Monocytes and radiation . . . ".
Abs. sheet of J. articles, ND: 91118015, Ti: "Endothelial expression of a mononuclear leukocyte . . . ".

*Primary Examiner*—John W. Rollins
*Assistant Examiner*—Nancy S. Carson
*Attorney, Agent, or Firm*—Sprung Horn Kramer & Woods

[57] ABSTRACT

A method of treating a patient to reduce or prevent an acute or chronic inflammation or an ischaemic state which comprises administering to such patient an effective amount therefor of efomycin A, E or G.

4 Claims, No Drawings

EFOMYCINS A, E AND G AS ANTIINFLAMMATORY AGENTS

The present invention relates to the use of the known natural substances efomycin A, E and G for the treatment of acute and chronic inflammations, especially to the use thereof as medicaments in the therapy of myocardial infarct.

It has already been disclosed that the natural substances efomycin A, E and G have an antibacterial effect on microorganisms in the rumen and can be employed as promoters of production and growth in veterinary medicine [cf. EP 197,360 and EP 236,894].

It has additionally been disclosed that efomycin E is, according to x-ray structural investigations, identical to the antibiotic elaiophylin [cf. Helv. Chim. Acta 64, 407–424 (1981); 65, 262–267], which has been published under the name azalomycin B in U.S. Pat. No. 3,076,746 with antibiotic and antimicrobial effect.

It has now been found that the natural substances efomycin A, E and G of the general formula (I)

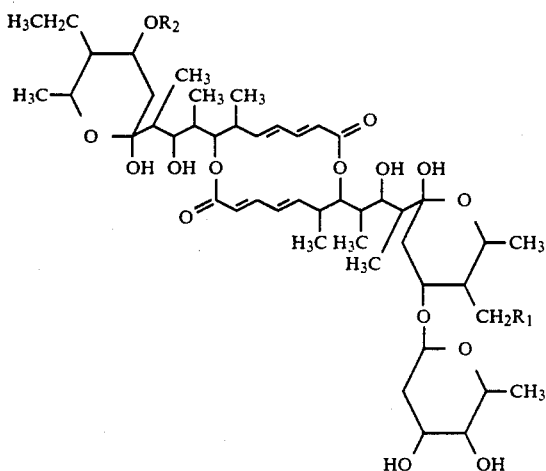

in which
R$^1$ represents methyl and
R$^2$ represents a radical of the formula

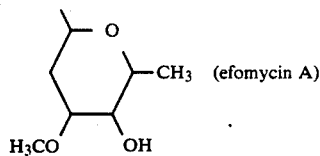 (efomycin A)

or
R$^1$ represents methyl and
R$^2$ represents a radical of the formula

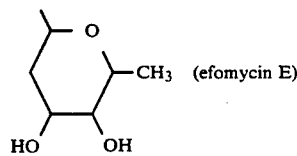 (efomycin E)

or
R$^1$ represents hydrogen and
R$^2$ represents a radical of the formula

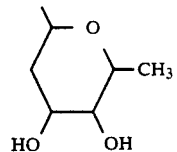 (efomycin G)

have, besides the known production- and growth-promoting, antibiotic and antimicrobial activities, surprisingly also an extremely strong inhibitory affect on the adhesion of leucocytes in acute and chronic inflammations and acute ischaemic states.

The detailed chemical and physical characterizations and the processes for preparing the compounds of the formula (I) to be used according to the invention have been disclosed [cf. EP 197,360 and EP 236,894].

The compounds of the formula (I) can be employed as active compounds in medicaments for acute and chronic inflammatory processes and/or an acute disturbance of blood flow (ischaemia).

Their effect consists initially in the reduction or complete inhibition of the adhesion of leucocytes to vascular endothelium and in the diminution or attenuation, associated therewith, of the subsequent undesired processes such as the release of oxygen free radicals (by polymorphonuclear neutrophilic leucocytes) or formation of foam cells (monocytes).

They are preferably suitable for the treatment and prevention of tissue necrosis after acute myocardial infarct. In addition, they can be used for the treatment and prevention of acute and chronic inflammations, not caused by infection, of the airways, such as allergic asthma, and for rheumatism, arteriosclerosis, osteoarthritis and inflammations of the gastrointestinal tract.

USED EXAMPLE 1

The substances according to the invention inhibit the adhesion of activated leucocytes to plastic surfaces.

The test is carried out on a microtiter plate. Each well is incubated with phosphate-buffered saline (PBS) in which 1% bovine serum albumin is dissolved for 30 min and then washed twice with PBS Aliquots of 100 μl of RPMI 1640 [RPMI 1640 medium with glutamine No. 041-01875 M Gibco Limited GB] medium which contains 10% fetal calf serum (FCS) and the substances to be tested are pipetted into the wells, and the plate is preincubated at 37° C. All further incubations are carried out under these conditions. The PMNs [polymorphonuclear neutrophilic leucocytes, isolated by the method of English et al., J. Immunol. Methods 5, 249–252 (1974)] are suspended in RPMI 1640 medium, and 2×10$^4$ cells in 50 μl are pipetted into each well. After incubation for 10 min the plates are shaken for 30 sec and the cells are activated with 50 μl of phorbol myristate acetate (final concentration 10$^{-6}$ mol/l). The mixture is then shaken for 30 sec, incubated for 1 hour, again shaken for 30 sec and the non-adherent cells are removed by washing twice with 300 μl of PBS each time. The adherent cells are lysed by adding 300 μl of 5% cetyltrimethylammonium bromide in 5 mM phosphate buffer pH 7.4, by shaking them at room temperature for 10 min.

The quantitative determination of the PMNs is carried out by measuring the myeloperoxidase activity. For this 270 μl of a mixture of phosphate buffer, 50 mM pH 6.0, ortho-dianisidine, 0.23 mg/ml, and $H_2O_2$, $10^{-4}$ mol/l, is added. The increase in extinction at 460 nm is measured 4 times at 2 min intervals.

TABLE 1

| | Inhibition of adhesion by efomycin A, E and G [%] |
|---|---|
| Control | 0 |
| efomycin E $5 \times 10^{-6}$ mol/l | 93 |
| efomycin E $10^{-6}$ mol/l | 62 |
| efomycin G $5 \times 10^{-6}$ mol/l | 95 |
| efomycin G $10^{-6}$ mol/l | 68 |
| efomycin A $5 \times 10^{-6}$ mol/l | 60 |
| efomycin A $10^{-6}$ mol/l | 25 |

USE EXAMPLE 2

The substance according to the invention also inhibit the adhesion of non-stimulated PMNL to activated endothelium.

1. PREPARATION OF THE CELL POPULATION

Human endothelium cells were obtained from umbilical cords by collagenase treatment and cultivated for 2–5 passages in medium with essential additives such as heparin and endothelial cell growth supplement. The cells were then detached by trypsin, inoculated in a density of $1-5 \times 10^4$ cells in microtiter plates and incubated for a further two days until confluence was reached.

Human polymorphonuclear granulocytes (PMNs) were prepared from fresh blood by sedimentation in 6% dextran sulphate followed by centrifugation through a Ficoll cushion and hypotonic lysis of the erythrocytes.

2. ADHESION TEST

Unstimulated PMNs in a concentration of $2.5-5 \times 10^5$ cells/well, and the test substances dissolved in DMSO, were added to the endothelial cells. After incubation for 30 minutes (37° C., 10% $CO_2$), non-specifically bound PMNs were removed by centrifugation of the inverted plate [cf. Charo et al., Blood, 65, 473–479 (1985)]. The number of PMNs bound to the endothelial cells was determined via the activity of the enzyme myeloperoxidase, which occurs in PMN but not in endothelial cells.

3. EFFECT OF THE SUBSTANCES Efo E AND Efo G

The test substances Efo E and Efo G were employed in a final concentration of $5 \times 10^{-6}$ mol/l in the measurement system described. The solvent concentration in the culture was then 0.1% DMSO.

PMN adhesion to the endothelium was reduced by 20 and 27% by Efo E and Efo G compared with the control without added substance (n=6, $p < 0.01$ and $p < 0.001$, respectively, by the t test). The solvent control with 0.1% DMSO revealed no significant change in the number of adherent PMNs.

USE EXAMPLE 3

HeLa 229 cells (ATCC CCL 2.1) were used in place of endothelial cells and were induced to adhere to the surface of a culture vessel. The adhesion of human PMNs to these cells can be inhibited dose-dependently by efomycins E and G.

TABLE 2

Inhibition of adhesion of leucocytes to HeLa cells by efomycins E and G.

| Control | 0[%] |
|---|---|
| efomycin E | |
| $1 \times 10^{-5}$ mol/l | 57 |
| $3.3 \times 10^{-6}$ mol/l | 45.4 |
| $1.1 \times 10^{-6}$ mol/l | 21.8 |
| $3.7 \times 10^{-7}$ mol/l | 13.3 |
| $1 \times 10^{-7}$ mol/l | 3.0 |
| efomycin G | |
| $1 \times 10^{-5}$ mol/l | 49.5 |
| $3.3 \times 10^{-6}$ mol/l | 32.6 |
| $1.1 \times 10^{-6}$ mol/l | 32.1 |
| $3.7 \times 10^{-7}$ mol/l | 4.4 |

USE EXAMPLE 4

The adhesion of leucocytes under ischaemic and non-ischaemic conditions in micro vessels can be quantified in the model of the hamster cheek pouch. The reduction in adhesion compared with the control by 1.0 mg/kg efomycin G i.v. is 40% under non-ischaemic conditions and 60% under ischaemic conditions. At this dose there is no observable effect on the blood pressure.

The new active compounds can be converted in a known manner into the customary formulations, such as tablets, coated tablets, pills, granules, aerosols, syrups, emulsions, suspensions and solutions, using inert, non-toxic, pharmaceutically suitable vehicles or solvents.

The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Administration is effected in the customary manner, preferably orally or parenterally, in particular perlingually or intravenously.

In general, it has proved advantageous, in the case of intravenous administration, to administer amounts of about 0.001 to 1 mg/kg, preferably about 0.01 to 0.5 mg/kg, body weight to achieve effective results, and in the case of oral administration, the dosage is about 0.01 to 20 mg/kg, preferably 0.1 to 10 mg/kg, body weight.

Nevertheless, it can at times be necessary to deviate from the amounts mentioned, and in particular to do so as a function of the body weight or of the nature of the administration method, of the individual behavior towards the medicament, or the nature of the formulation and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day.

It will be appreciated that the instant specification is set forth by way of illustration and not limitation, and that various modifications and changes may be made without departing from the spirit and scope of the present invention.

What is claimed is:

1. A method of inhibiting the adhesion of leukocytes to vascular endothelial cells which comprises treating such cells with an effective amount therefore of a compound of the formula

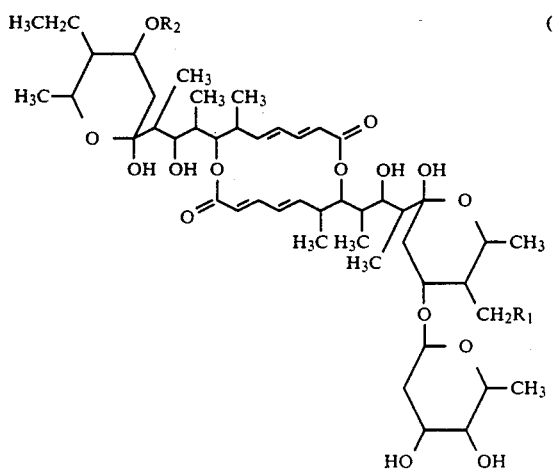 (I)

in which

R¹ represents methyl and

R² represents a radical of the formula

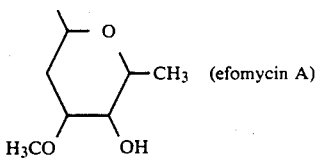 (efomycin A)

or

R¹ represents methyl and

R² represents a radical of the formula

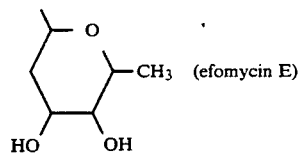 (efomycin E)

or

R¹ represents hydrogen and

R² represents a radical of the formula

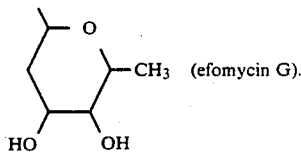 (efomycin G).

2. The method according to claim 1, wherein the compound is efomycin A.

3. The method according to claim 1, wherein the compound is efomycin E.

4. The method according to claim 1, wherein the compound is efomycin G.

* * * * *